United States Patent [19]
Ozawa et al.

[11] Patent Number: 6,159,624
[45] Date of Patent: Dec. 12, 2000

[54] HIGH-PROTON-CONDUCTIVE ANTIMONIC ACID FILM

[75] Inventors: Kiyoshi Ozawa; Yoshio Sakka; Tetsuo Uchikoshi; Muneyuki Amano, all of Ibaraki, Japan

[73] Assignee: National Research Institute for Metals, Ibaraki, Japan

[21] Appl. No.: 08/938,521

[22] Filed: Sep. 26, 1997

[30] Foreign Application Priority Data

Jan. 22, 1997 [JP] Japan ................................. 9-009546

[51] Int. Cl.$^7$ ........................................ B32B 9/00
[52] U.S. Cl. ........................................ 428/689; 428/221
[58] Field of Search .................... 428/221, 689

[56] References Cited

PUBLICATIONS

Abstracts of the Japan Institute of Metals, p. 188, Sep. 28, 1996.

Primary Examiner—Bernard Pianalto
Attorney, Agent, or Firm—Wenderoth, Lind & Ponack, L.L.P.

[57] ABSTRACT

To provide an antimonic acid film having an excellent conductivity and a high response to humidity, and useful as a high-performance humidity sensor, a hydrogen gas sensor or a hydrogen fuel cell, the present invention provides an antimonic acid film comprising single crystals of cubic antimonic acid dispersed in amorphous antimonic acid by causing metallic antimony or an oxygen-containing compound thereof to react with hydrogen peroxide using the resultant reaction solution as the raw material, and forming a film on an insulated substrate.

2 Claims, 6 Drawing Sheets

HIGH-PROTON-CONDUCTIVE ANTIMONIC ACID FILM

FIELD OF THE INVENTION

The present invention relates to a high-proton-conductive film and a manufacturing method thereof. More particularly, the present invention relates to a high-proton-conductive antimonic acid film useful as a high-performance humidity sensor, a hydrogen gas sensor or a hydrogen fuel cell.

RELATED ART

There is conventionally known a method of synthesizing antimonic acid through hydrolysis of mainly antimony pentachloride ($SbCl_6$). The resultant antimonic acid has properties as a proton-conductive substance, generally represented by $Sb_2O_6 \cdot nH_2O$, where the n-value is dependent on the degree of absorption of steam in the open air, or reversely, on the degree of drying, and is considered to take a value of about 2 to 4 in the case, for example, of vacuum drying.

However, antimonic acid available by the conventional method is in the form of particulates. When actually using it as a proton-conductive substance, it is necessary to manufacture a compressed form of particulates or manufacture a slurry by dispersing the particulates in an appropriate solvent, and form a coated film on a substrate. The proton-conductive sample thus manufactured has a low density and requires a difficult grain boundary control. There is therefore a limit in improving proton conductivity, and the material has problems such as a low response of conductivity to humidity.

The present invention has an object to overcome the foregoing technical limit, and provide a novel antimonic acid film having an excellent proton conductivity and a high response to humidity and a novel method of manufacturing the same.

SUMMARY OF THE INVENTION

As means to achieve the foregoing object, the present invention provides a high-proton-conductive antimonic acid film comprising single crystals of cubic antimonic acid dispersed in amorphous antimonic acid. The invention provides also a high-proton-conductive antimonic acid film comprising an oriented film of cubic antimonic acid.

Further, the invention provides a method of manufacturing a high-proton-conductive antimonic acid film comprising the steps of causing metallic antimony or an oxygen-containing compound thereof to react with a hydrogen peroxide solution, coating the resultant reaction solution onto an insulated substrate, and drying the same or further heating the antimonic acid film.

●: (lll)-oriented film of cubic antimonic acid

○: Slurry coated film of cubic antimonic acid powder

DETAILED DESCRIPTION OF THE INVENTION

As described above, the invention provides a high-proton-conductive antimonic acid film. As to embodiment of the invention, the method of the invention is particularly characterized in the use of a reaction solution of metallic antimony or an oxygen-containing compound thereof and hydrogen peroxide for film formation.

The oxygen-containing compound in this case may be an inorganic compound or an organic compound including an oxide, alkoxide, an organic acid salt such as a carboxylic salt, or an organic complex compound. For the reaction with hydrogen peroxide, reaction is caused with an appropriate mole ratio of hydrogen peroxide of about 0.2 to 10 times, and the reaction solution is used after removal of solid residues.

The reaction temperature is within a range of from about −10 to 150° C.; it should preferably be within a range of from about the room temperature to 150° C. when metallic antimony is used as the material, and from about 0 to 50° C. when an oxygen-containing compound is used as the material.

Film forming is accomplished by coating with appropriate means such as spin coating or dip coating.

The thickness of the thus produced coated film is controlled in response to this means.

Coating is effected onto an insulted substrate. The material for the substrate may be glass or alumina.

More specifically, the invention provides, as described in the following examples, an antimonic acid film in which single crystals of cubic antimonic acid are dispersed in amorphous antimonic acid or an oriented film of cubic antimonic acid.

Now, the present invention will be described further in detail by means of examples

EXAMPLES

Example 1

Metallic antimony powder in an amount of 3 g was caused to react with 50 ml of hydrogen peroxide solution (31%) at 100° C. for 24 hours. The reaction product was filtered and thus was used as the raw material solution for forming a film. Using this solution, a film was formed on a glass substrate by spin coating (revolutions: 3,000 rpm), and dried at the room temperature.

Figure 1A:
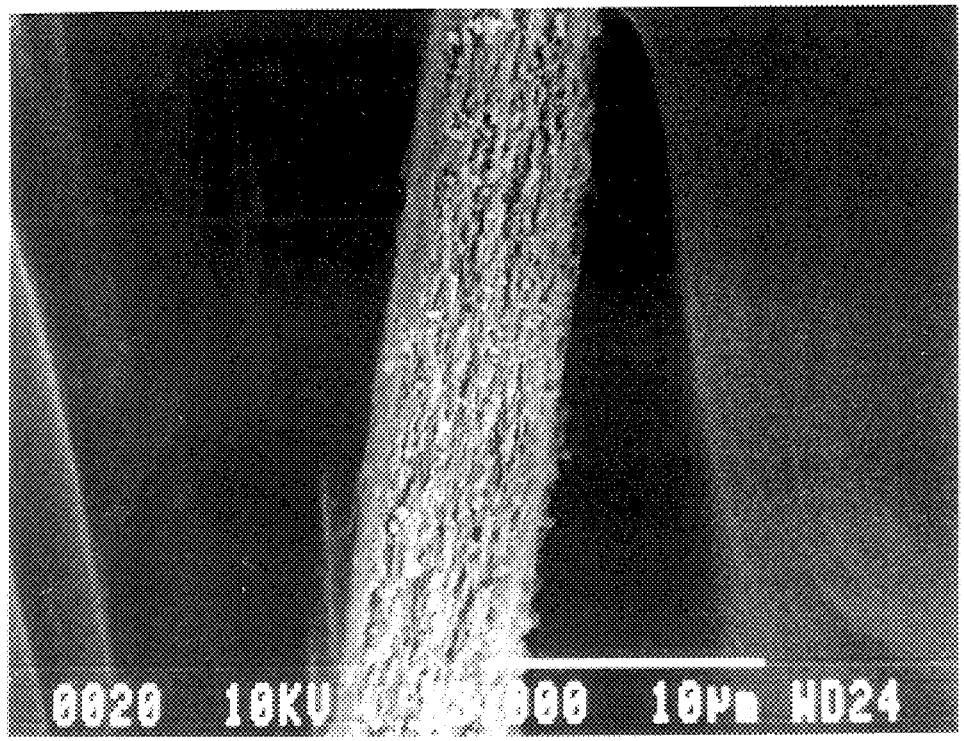
FIG. 1 is a scanning electron microscope (SEM) photographs of an antimonic acid film in the Example 1: (a) and (b) are sectional views.
Figure 1B:
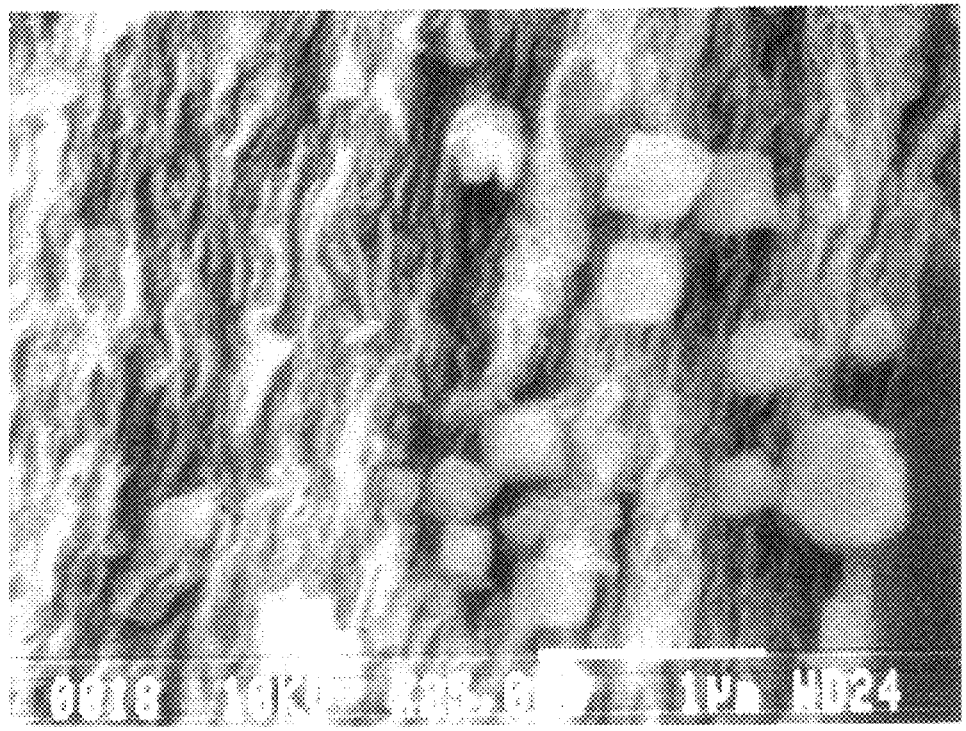

FIGS. 1(a) and 1(b) shows SEM photographs of sectional views of the produced antimonate film.

As shown in FIGS. 1(a) and 1(b), the antimonic acid film had a structure in which single crystals of cubic antimonic acid were dispersed in amorphous antimonic acid.

Figure 2:
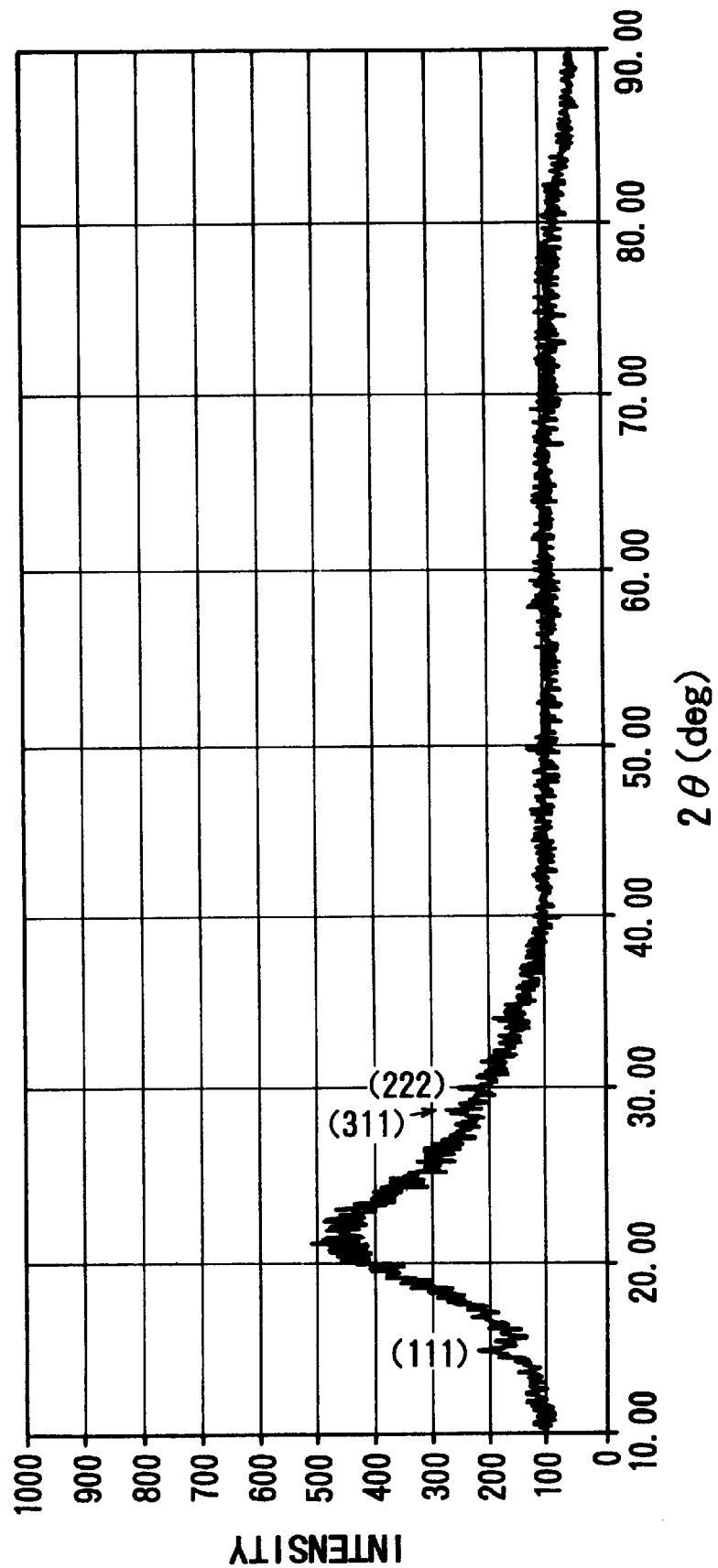
FIG. 2 illustrates X-ray diffraction pattern of the antimonic acid film of the Example 1 having a structure in which single crystals of cubic antimonic acid are dispersed in amorphous antimonic acid.
Figure 3:
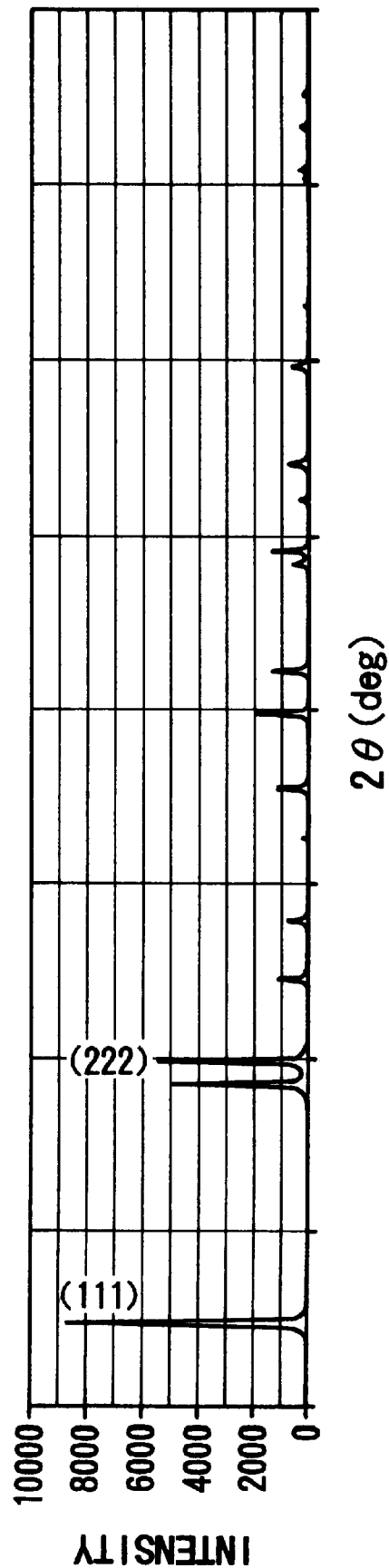
FIG. 3 illustrates X-ray diffraction pattern of a commercially available cubic antimonic acid powder for comparison.

FIG. 2 illustrates X-ray diffraction pattern of the foregoing antimonate film having the structure in which single crystals of cubic antimonic acid are dispersed in amorphous antimonic acid; and FIG. 3 illustrates X-ray diffraction pattern for a commercially available cubic antimonic acid powder for comparison purposes.

The n-value for $SB_2O_5 \cdot nH_2O$ as the composition of the antimonic acid film was confirmed to be n=3.4 for amorphous antimonic acid, and n=3.1 for cubic antimonic acid, both immediately after vacuum drying ($10^{-3}$ Pa) at the room temperature.

Further, proton conductivity of the foregoing antimonic acid film was measured. The antimonic acid film used for measurement of proton conductivity was one having a thickness of about 1 μm achieved by repeating five runs of spin coating. For this measurement, a method known as the AC complex impedance measuring method comprising the steps of measuring impedance in the range of from 100 Hz to 10 MHz, drawing Cole-Cole plots and determining a resistance value of the sample was employed. In this method, not only the proton conductivity of the sample, but also conductivity including also electron conductivity are measured. The resultant value is not therefore accurately a pure proton conductivity. For antimonic acid, however, proton conductivity accounts for the most past of conductivity thereof, and adopting the thus resulting conductivity as the proton conductivity for that antimonic acid poses no problem.

In the above-mentioned measurement of proton conductivity of the antimonic acid film, the value was compared with proton conductivity of a slurry coated film of cubic antimonic acid powder as a comparative sample.

The slurry coated film cubic antimonic acid powder as the comparative sample was prepared by making a slurry by dispersing a commercially available cubic antimonic acid powder in water, coating the resultant slurry onto a glass substrate, and drying the same by vacuum drying ($10^{-3}$ Pa).

Proton conductivity of the foregoing antimonic acid film in the example of the invention showed a level within a range of from $10^{-4}\Omega^{-1}$ cm$^{-1}$ to $10^{-3}\Omega^{-1}$ cm$^{-1}$ within a range of relative humidity of from 0 to 1, which was up to three digits as large as that for the slurry coated film of cubic antimonic acid powder.

Example 2

The antimonic acid film produced in the Example 1 was further heated at 120° C., resulting in a (111)-oriented film of cubic antimonic acid.

Figure 4:
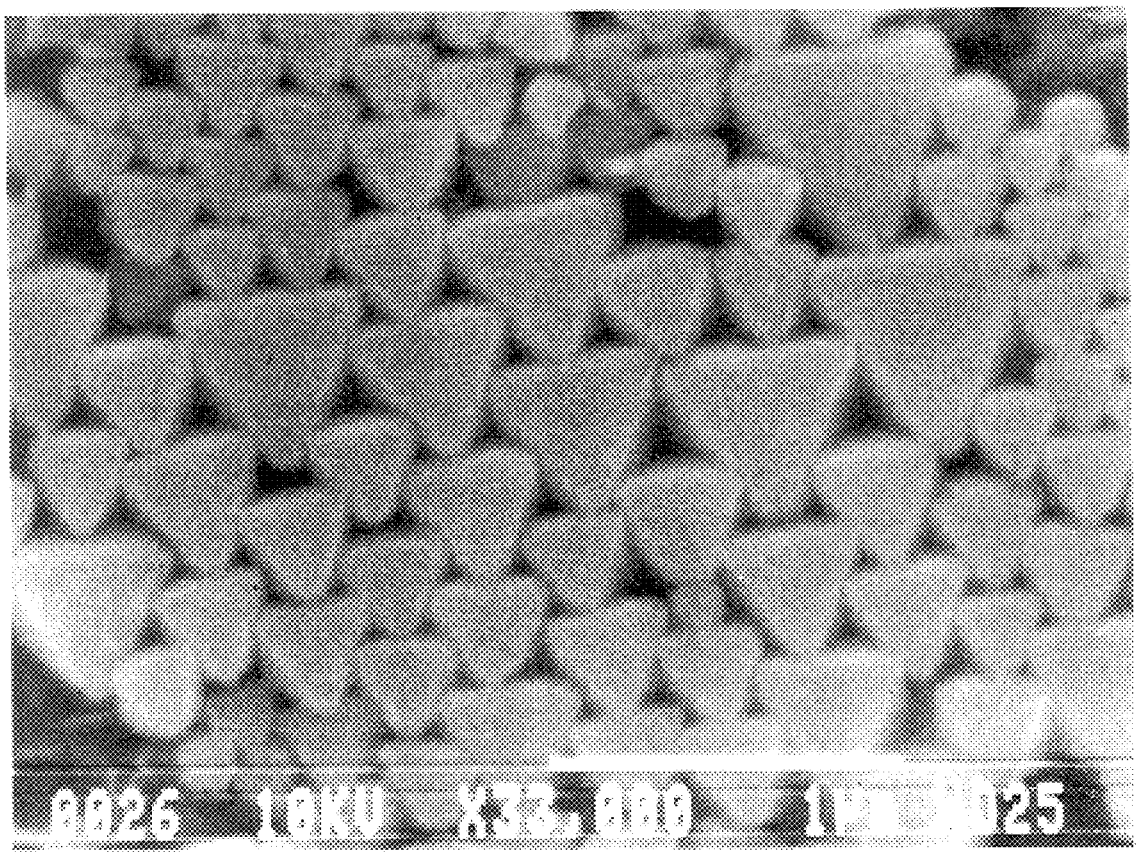
FIG. 4 is SEM photograph of a (lll)-oriented film of cubic antimonic acid of the Example 2.
Figure 5:
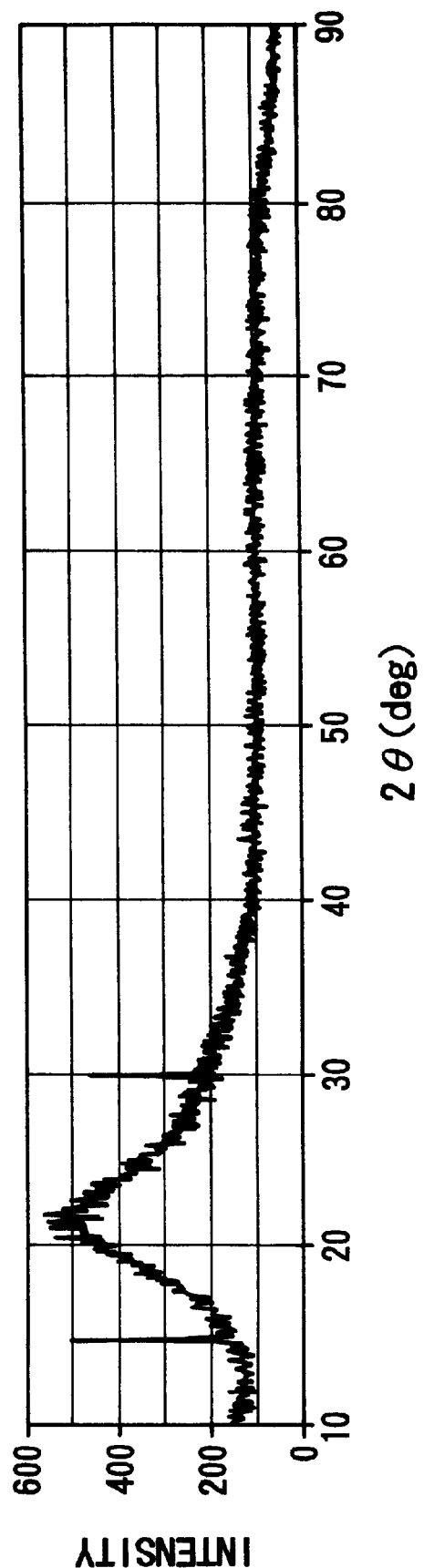
FIG. 5 illustrates X-ray diffraction pattern of a (lll)-oriented film of cubic antimonic acid.

FIG. 4 illustrates an SEM photograph of a (111)-oriented film surface of cubic antimonic acid; and FIG. 5 illustrates X-ray diffraction pattern of the (111)-oriented film of cubic antimonic acid.

Figure 6:
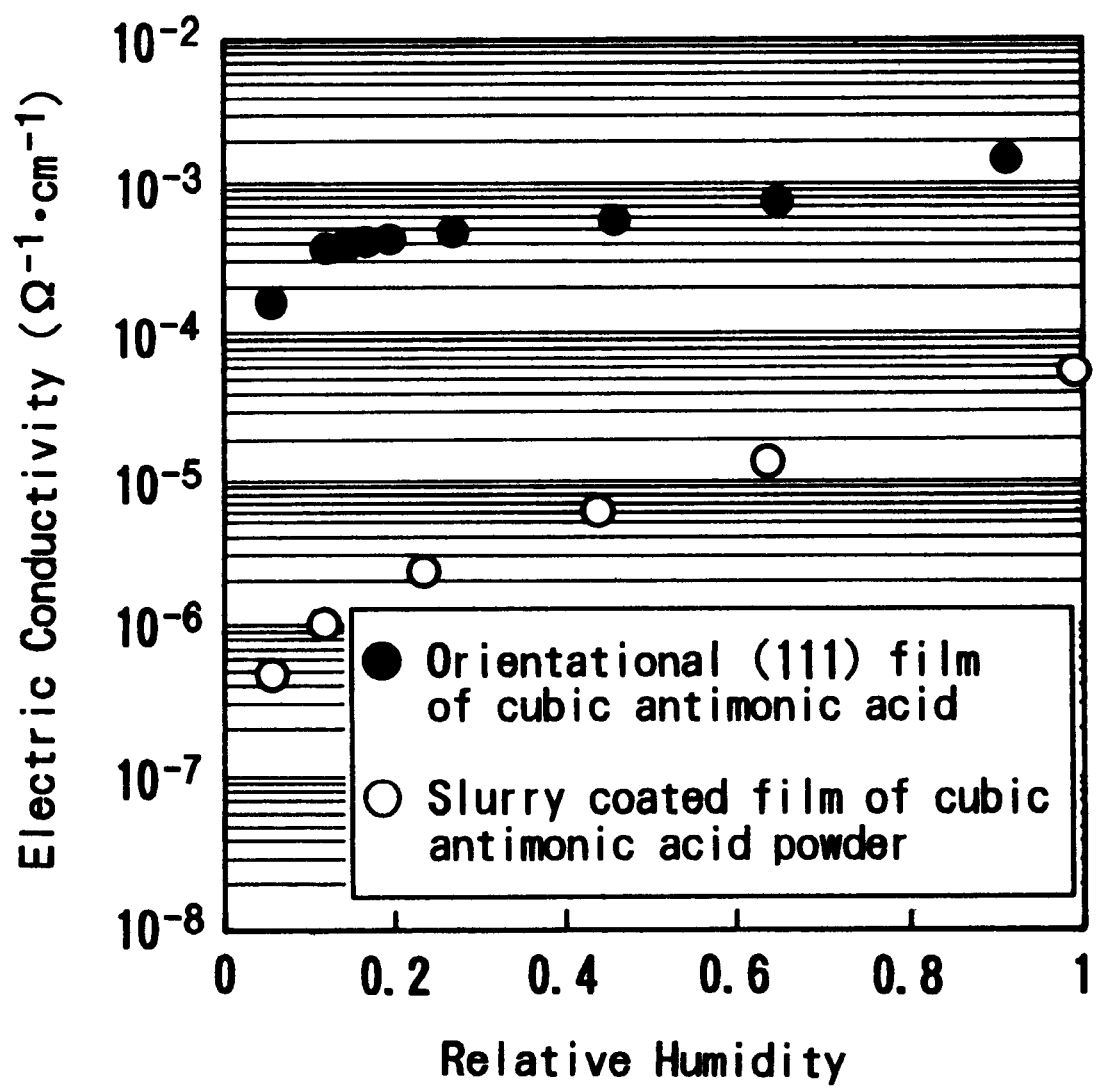
FIG. 6 shows relative humidity dependence of the proton conductivity of the (lll)-oriented film of cubic antimonic acid and the slurry coated film of commercially available cubic antimonic acid powder.

Proton conductivity of the resultant (111)-oriented film of cubic antimonic acid was measured in the same manner as in the Example 1, and the result as shown in FIG. 6 was obtained. The result showed substantially the same value as for the antimonic acid film before heating in the Example 1. Only, the film in the Example 2 was more excellent in response to humidity.

Example 3

Antimony propoxide in an amount of 5 g was caused to react with 50 ml of hydrogen peroxide solution (31%) at 0° C. for 24 hours. Then, organic residues were removed by extraction with diethyl ether, and after filtration, the filtrate was used as the raw material for film forming. The solution was coated onto an alumina substrate for form a film, and the resultant film was dried at the room temperature. An antimonic acid film having substantially the same structure as that of the antimonic acid film obtained in the Example 1 was obtained.

The ratio of single crystals in the resultant antimonic acid film was smaller than that in the Example 1, but proton conductivity showed a value larger by about a digit than that of the slurry coated film of commercially available cubic antimonic acid powder used for comparison purposes in the Example 1.

According to the present invention, as described above in detail, there is provided an antimonic acid film having an excellent conductivity and a high response to humidity. This makes it possible to provide a higher-performance humidity sensor. Because of the excellent chemical durability of antimonic acid itself, it is applicable in an acidic or alkaline atmosphere.

What is claimed is:

1. A high-proton-conductive antimonic acid film comprising single crystals of cubic antimonic acid dispersed in amorphous antimonic acid.

2. A high-proton-conductive antimonic acid film comprising an oriented film of cubic antimonic acid.

\* \* \* \* \*